US00PP08822P

United States Patent [19]

De Meyer

[11] Patent Number: Plant 8,822

[45] Date of Patent: Jul. 5, 1994

[54] GUZMANIA PLANT NAMED ORIENTAL

[75] Inventor: Henri De Meyer, Destelbergen, Belgium

[73] Assignee: H. De Meyer - De Rouck, Laarne, Belgium

[21] Appl. No.: 104,506

[22] Filed: Aug. 9, 1993

[51] Int. Cl.[5] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Foley & Lardner

[57] ABSTRACT

A new and distinct cultivar of Guzmania plant named Oriental, characterized particularly by the coloration of its bracts. The bracts at the bottom of the flower shaft are mainly green with a red merge zone and a green tip. The intermediate bracts are mainly orange with an outer red merge zone and tip. The uppermost bracts surrounding the flowers, which are yellow-orange with a very bright yellow tip, are orange with red at the very tip.

2 Drawing Sheets

The present invention comprises a new and distinct cultivar of *Guzmania lingulata*, referred to by the name Oriental. The genus Guzmania is within the family Bromeliaceae.

Oriental is a product of a planned selecting and in-breeding program conducted in Laarne, Belgium. The program evolved from the importation by the inventor of seeds of several different cultivars of *Guzmania lingulata* from Colombia, South American. When grown out to flower, several plants were selected for their beautiful flowers, and were subsequently crossed with cultivars from the same species (in-breeding).

Oriental was originated by the inventor Henri De Meyer in Laarne, Belgium, from the in-breeding program referred to. The male and female parents were *lingulata* plants which are unknown at this time. Selections were made from the progeny of the stated cross for purposes of further breeding.

The progenitor of Oriental was discovered and selected by the inventor after flowering near the end of the 1970s. The selected cultivars were thereafter inbred over several generations, resulting in the new cultivar Oriental.

Oriental was first asexually reproduced in 1988 by offshoots by the inventor in Laarne, Belgium. The offshoots were rooted, with the resulting plantlets being detached from the mother plant and potted up in an appropriate growing mixture. Asexual reproduction by tissue culture techniques has been effected for the past three years. Horticulatural examination of plants so propagated has demonstrated that the combination of characteristics as herein disclosed for Oriental are firmly fixed and retained through successive generations of asexual reproduction, which can be effected by offshoots as described or by known tissue culture techniques.

The accompanying color photographic drawings show typical flower, bract and foliage characteristics of Oriental, with colors being as true as possible with illustrations of this type.

The photograph on sheet 1 is a top perspective view of a typical plant of Oriental, in flower.

The photo on sheet 2 comprises a closeup view showing the flowers and surrounding bracts in more detail.

Oriental has not been observed under all possible environmental conditions. The phenotype may vary significantly when grown under different conditions of temperature, light and other determining factors, without, however, any variation in the genotype. The following observations, measurements and comparisons describe plants grown in Laarne, Belgium under greenhouse conditions which approximate those generally used in commercial practice.

Classification:

*Botanical.*—*Guzmania lingulata* cv. Oriental.

PLANT

Form: Rosette.

Height: Approx. 15–18 cm when plant is in bloom; leaf rosette approx. 11–12 cm.

Diameter: Approx. 45 cm when plant is in bloom.

Growth habit: Stemless.

Method of propagation: Offshoots or tissue culture.

Foliage:

*Quantity.*—Approximately 20 leaves.

*Size of leaves.*—Length of 5 to 28 cm depending on whether leaves are at top or bottom.

*Shape of leaf.*—Linear with a pointed tip (becomes lanceolate where the leaves curl inward, approximately 6–7 cm from the leaf tip); leaf edge entire and upright.

*Surface texture.*—Slightly ribbed (both bottom and top surfaces).

*Color.*—Upperside 147 A. Underside 147 A with very fine purplish stripes on the lower half of the leaf, 184A. The stripes can be so close together that the underside of the leaf appears to be 184A.

*Leaf sheaths.*—Size: Width 5 cm, length 8 cm. Shape: Oval. Color: The part of the leaf sheath which is covered by other leaf sheaths is 162C. The part of the leaf sheath which is clearly visible from outside is approximately 147A, similar to the foliage color.

BRACTS

Quantity: About 25 in number, with the bases of the bracts completely surrounding the flower shaft.

Size: Bracts at bottom of the flower shaft are approximately 16 to 22 cm in length and 20 to 22 mm in width. Bracts near the top of the flower shaft have a length of 9 to 12 cm and a width of 12 to 15 mm.

Shape: The leaf curls outward so that the bracts of one and the same verticil form a generally horizontal plane. The bracts at the bottom of the flower shaft spread out wider but do not reach the same height as the horizontal plane of the bracts in the center.

Color: The lowermost verticil of bracts have a green tip 147A with a red merge zone (closest to 43A) and a green tip. Nearest to the flower shaft the main color of the bracts is 24A. The red merge zone moves outwardly on approaching the upper bracts while the green tip disappears. The upper bracts in the center are 24A with an orange-red tip nearest to 33A.

FLOWERS

Borne: On a short and sturdy shaft which stands erect and has a diameter of approximately 2.5 cm and a length of about 8 cm.

Blooming habit: Flowers bloom approximately 12 weeks after induction. Single flowers bloom only one day. The total inflorescence (from first to last flower) lasts about 6 weeks.

Quantity: 12 to 25 total flowers.

Size: The entire flower system has a length of approximately 7 cm and a diameter of 2 cm. Each individual flower is about 4–5 cm in length.

Shape: Straight.

Color: Yellow-orange approximately 24A with a light yellow white top 11D of approximately 5 mm.

Petals: 3 in number; lower part 24A and upper part 11D.

Reproductive organs.

*Pistils.*—1, white.

*Stamen.*—6, white.

I claim:

1. A new and distinct cultivar of Guzmania plant named Oriental, as illustrated and described.

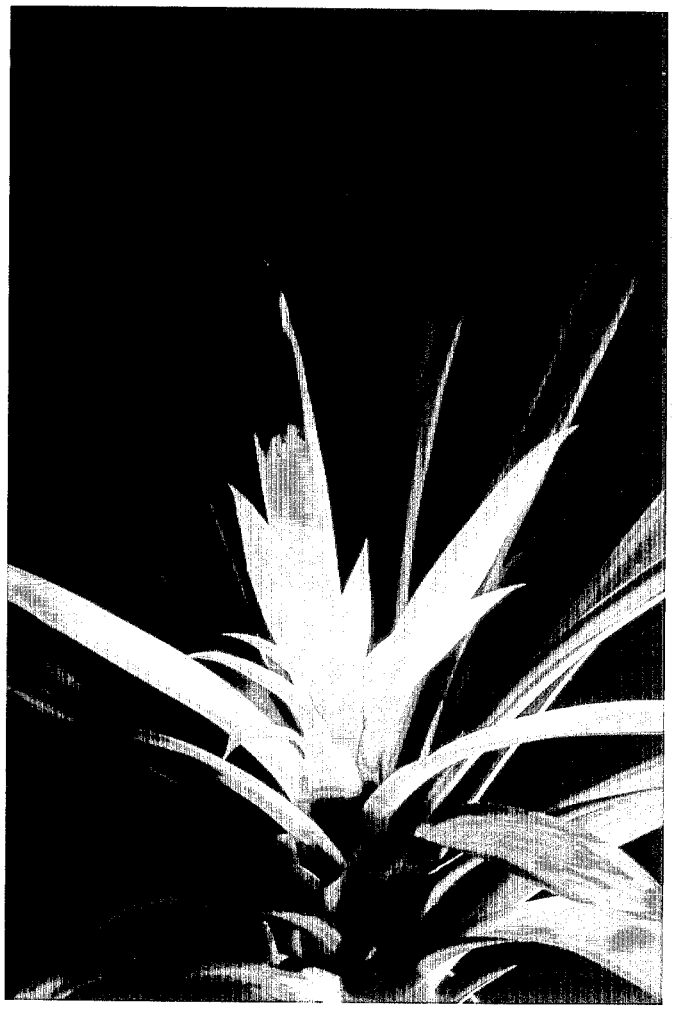

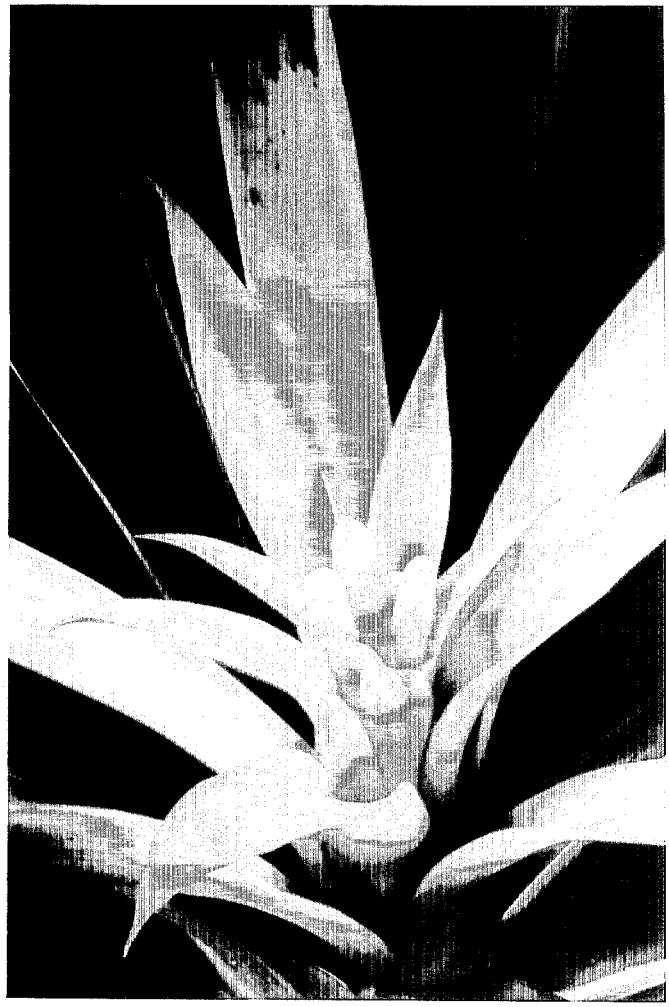

* * * * *